(12) United States Patent
Oldham et al.

(10) Patent No.: US 7,407,798 B2
(45) Date of Patent: Aug. 5, 2008

(54) LENS ASSEMBLY FOR BIOLOGICAL TESTING

(75) Inventors: Mark F. Oldham, Los Gatos, CA (US); Richard T. Reel, Hayward, CA (US); Steven J. Boege, San Mateo, CA (US)

(73) Assignee: Applera Corporation, Foster City, CA (US)

( * ) Notice: Subject to any disclaimer, the term of this patent is extended or adjusted under 35 U.S.C. 154(b) by 517 days.

(21) Appl. No.: 11/096,341

(22) Filed: Mar. 31, 2005

(65) Prior Publication Data

US 2005/0170495 A1 Aug. 4, 2005

Related U.S. Application Data

(63) Continuation-in-part of application No. 10/146,066, filed on May 16, 2002, now Pat. No. 6,982,166.

(51) Int. Cl.
*G01N 21/00* (2006.01)
*C12M 1/34* (2006.01)

(52) U.S. Cl. .................. 435/288.7; 422/82.05

(58) Field of Classification Search .............. 435/288.7; 422/82.05
See application file for complete search history.

(56) References Cited

U.S. PATENT DOCUMENTS

| | | | |
|---|---|---|---|
| 5,096,807 A * | 3/1992 | Leaback | 435/6 |
| 5,234,665 A | 8/1993 | Ohta et al. | |
| 5,315,375 A | 5/1994 | Allen | |
| 5,682,232 A | 10/1997 | Tajima et al. | |
| 5,734,496 A | 3/1998 | Beach | |
| 5,774,214 A | 6/1998 | Prettyjohns | |
| 5,780,857 A | 7/1998 | Harju et al. | |
| 5,892,577 A | 4/1999 | Gordon | |
| 5,928,907 A | 7/1999 | Woudenberg et al. | |
| 5,961,926 A | 10/1999 | Kolb et al. | |
| 5,993,746 A | 11/1999 | Priha et al. | |
| 6,008,892 A | 12/1999 | Kain et al. | |
| 6,015,674 A | 1/2000 | Woudenberg et al. | |
| 6,024,920 A | 2/2000 | Cunanan | |
| 6,027,695 A | 2/2000 | Oldenburg et al. | |
| 6,033,605 A | 3/2000 | Szlosek | |
| 6,130,745 A | 10/2000 | Manian et al. | |

(Continued)

FOREIGN PATENT DOCUMENTS

WO 95/30139 11/1995

(Continued)

OTHER PUBLICATIONS

Cohn, Robert W., et al., "Fully Complex Diffractive Optics by Means of Patterned Diffuser Arrays: encoding Concept and Implications for Fabrication," *J. Opt. Soc. Am. A*, May 1997, 1110-1123, vol. 14, No. 5.

(Continued)

*Primary Examiner*—Walter D. Griffin
*Assistant Examiner*—Lydia Edwards (57) ABSTRACT

The invention relates to an optical detection system for a thermal cycling device including at least one light source, a light detection device for detecting light received from a plurality of biological samples, and a lens having a plurality of focusing lens segments greater than the plurality of biological samples to direct light into the plurality of biological samples.

20 Claims, 10 Drawing Sheets

U.S. PATENT DOCUMENTS

| | | | |
|---|---|---|---|
| 6,232,114 B1 | 5/2001 | Coassin et al. | |
| 6,238,911 B1 | 5/2001 | Kasahara | |
| 6,246,525 B1 | 6/2001 | Ikami | |
| 6,256,088 B1 | 7/2001 | Gordon | |
| 6,258,326 B1 | 7/2001 | Modlin | |
| 6,271,972 B1 | 8/2001 | Kedar et al. | |
| 6,272,939 B1 | 8/2001 | Frye et al. | |
| 6,280,960 B1 * | 8/2001 | Carr | 435/7.2 |
| 6,304,378 B1 * | 10/2001 | Clausen | 359/456 |
| 6,330,017 B1 | 12/2001 | Suzuki | |
| 6,366,405 B2 | 4/2002 | Abe | |
| 6,381,072 B1 | 4/2002 | Burger | |
| 6,399,952 B1 | 6/2002 | Maher et al. | |
| 6,437,345 B1 * | 8/2002 | Bruno-Raimondi et al. | 250/458.1 |
| 6,514,750 B2 | 2/2003 | Bordenkircher et al. | |
| 6,818,437 B1 * | 11/2004 | Gambini et al. | 435/288.7 |
| 6,942,836 B2 | 9/2005 | Freudenthal et al. | |

FOREIGN PATENT DOCUMENTS

| | | |
|---|---|---|
| WO | 97/36681 | 10/1997 |
| WO | 98/10314 | 3/1998 |
| WO | 99/60381 | 11/1999 |
| WO | 00/22417 | 4/2000 |
| WO | 00/25922 | 5/2000 |
| WO | 01/28684 | 4/2001 |
| WO | 01/35079 | 5/2001 |

OTHER PUBLICATIONS

Yasuhiro Tanaka, et al., "Diffractive-Refractive Achromatic Lens for Optical Disk System by Glass Molding," *Optical Review*, 1998, 334-339, vol. 5, No. 6.

* cited by examiner

LENS ASSEMBLY FOR BIOLOGICAL TESTING

PRIORITY

This application claims the benefit as a continuation-in-part from U.S. Ser. No. 10/146,066, filed on May 16, 2002 and is incorporated herein by reference.

FIELD

The present invention relates to an optical system for focusing light onto one or more samples in a system for biological testing. In one aspect, the invention relates to a lens assembly having the functions of collimating and focusing light onto one or more samples integrated into the lens assembly.

BACKGROUND

Biological testing has become an important tool in detecting and monitoring diseases. In the biological testing field, thermal cycling is used to amplify nucleic acids by, for example, performing PCR and other reactions. PCR in particular has become a valuable research tool with applications such as cloning, analysis of genetic expression, DNA sequencing, and drug discovery.

Recent developments in the field have spurred growth in the number of tests that are performed. One method for increasing the throughput of such biological testing is to provide real-time detection capability during thermal cycling. Real-time detection increases the efficiency of the biological testing because the characteristics of the samples can be detected while the sample well tray remains positioned in the thermal cycling device.

In a real-time detection system testing may be performed on multiple samples during a cycle of the testing device. With this type of system, light may be emitted from a light source to be absorbed and re-emitted as fluorescence by the biological sample(s) and ultimately may be detected or collected by a light detecting device such as a camera or CCD, for example. To assist in the focusing the light into the samples and collecting the light out of the samples toward detecting device, one or more lenses may be provided.

One of the drawbacks of conventional devices utilizing lens assemblies in conjunction with multiple sample testing devices is the complexity of the lens(es). It may often be desirable to have a lens for collimating light so that it may be properly aligned with a row or column of sample wells in a sample well tray. To further enhance the testing process, an additional lens assembly may be provided for focusing light more precisely within each of the sample wells. These focusing lens assemblies often may comprise a plurality of non-integral components.

SUMMARY

In accordance with the invention, an optical detection system for a thermal cycling device is disclosed including at least one light source, a light detection device for detecting light received from a plurality of biological samples, and a lens having first and second surfaces formed on the lens, the second surface substantially opposed to the first surface. The first surface may be configured to substantially collimate light and the second surface may be configured to direct light into each of the plurality of biological samples.

According to another aspect, the second surface may comprise a matrix of lenses formed into the second surface and the matrix may comprise a plurality of focusing lens portions.

According to yet another aspect, a plurality of focusing lens portions may correspond to a plurality of biological samples.

In another aspect, the matrix may comprise 4, 8, 12, 24, 48, 96, 384, 768, 1536, 3072, 6144 or more focusing lens portions.

In yet another aspect, the system may further include a sample block assembly configured to receive a sample well tray.

In yet a further aspect, the sample block assembly may be configured to receive the lens.

In another aspect, the sample block assembly may include a heated cover configured to receive the lens.

In yet another aspect, the lens may be mounted to the sample block assembly with at least one fastening device.

According to another aspect, the fastening device may comprise one of a clip-fastening device, a clamp-fastening device, and a screw-fastening device.

According to yet another aspect, the heated cover and the sample block assembly may be configured to heat the biological samples to a temperature of approximately 80° C. or greater and the lens may comprise a material configured to operate up to a temperature of at least 80° C.

According to another aspect, the lens material may comprise a non-fluorescing clear polycarbonate.

In another aspect, the sample block assembly may be configured to heat the sample tray assembly to a temperature of approximately 60° C. and the lens may comprise a material configured to operate up to a temperature of at least 60° C.

In yet another aspect, the lens material may be chosen from acrylics, molted glass, styrenes, polyethylenes, polycarbonates, and polypropylenes.

According to another aspect, the first lens surface and the second lens surface may be integrally formed by at least one of injection molding, reactive ion etching, compression molding, stamping, hot embossing, and melting with surface tension.

According to yet another aspect, a plurality of focusing lens portions may be configured to direct light of an approximately equal intensity into a plurality of biological samples.

According to a further aspect, one or more of the plurality of focusing lens portions may be configured to allow differing light intensity to pass through than at least one other of the plurality of focusing lens portions.

In another aspect, the one or more of the plurality of focusing lens portions comprises a smaller focusing lens portion than at least one other of the plurality of focusing lens portions.

In yet another aspect, part of the one or more of the plurality of focusing lens portions may be masked to differ the intensity of light passing through the one or more of the plurality of focusing lens portions.

In another aspect, the first lens surface may comprise a Fresnel lens, lenses of different focal lengths, or diffractive elements such as lenses, gratings, or Fresnel zone plates. In another aspect, the first lens surface can include holographic elements.

In yet another aspect, the at least one light source may provide light of a non-uniform intensity across one surface, and another surface may be configured to provide light at approximately uniform intensity to each of the plurality of biological samples.

According to another aspect, biological samples may have corresponding focusing lens segments.

In another aspect, lens for an optical detection system of a thermal cycling device is disclosed. The lens may include a collimating surface and a matrix surface substantially opposed to the first lens surface and the matrix surface may include a plurality of focusing lens segments. The collimating surface may be configured to substantially collimate light from a light source, and the plurality of focusing lens segments may be configured to direct light into a plurality of biological samples.

In yet another aspect, the collimating surface and the matrix surface may be integrally formed by at least one of injection molding, reactive ion etching, compression molding, stamping, hot embossing, and melting with surface tension.

According to another aspect, each of the plurality of focusing lens segments may be configured to direct light at an approximately equal intensity.

According to yet another aspect, one or more of the plurality of focusing lens segments may be configured to allow differing intensities of light to pass through than at least one other of the plurality of focusing lens segments.

In another aspect, the one or more of the plurality of focusing lens segments may comprise a smaller focusing lens segment than at least one other of the plurality of focusing lens segments.

In yet another aspect, a portion of the one or more focusing lens segments may be masked to differ the intensity of light passing through the one or more of the focusing lens segments.

In a further aspect, the lens may comprise 4, 8, 12, 24, 48, 96, 384, 768, 1536, 3072, 6144 or more focusing lens segments.

According to another aspect, the lens may comprise a one-piece lens.

In another aspect, an optical detection system for a thermal cycling device is disclosed, the system may include at least one light source, a light detection device for detecting light received from a plurality of biological samples, a lens body having a first surface formed into the lens body and a second surface formed into the other side of the body, and a sample block assembly configured to receive a sample well tray. The sample well tray may be configured to contain the plurality of biological samples and the sample block assembly may include a heated cover configured to receive the lens. Further, the first surface may be configured to substantially collimate light and the second surface may comprise a lens matrix having a plurality of focusing lens portions configured to direct light into each of the plurality of biological samples.

According to yet another aspect, a method of testing a plurality of biological samples is disclosed. The method may include providing light from at least one light source, providing a light detection device for detecting light received from the plurality of biological samples, providing a lens having a collimating lens portion formed on a first surface of the lens and a matrix of focusing lens portions formed on a second surface of the lens with the first surface substantially opposed to the second surface. Light may pass through the collimating and focusing lens portions into the plurality of biological samples and may be detected by the detection device.

Other aspects still will become apparent from the detailed description that follows. It should be understood that the invention, in its broadest sense, could be practiced without accomplishing one or more of the aspects described herein.

BRIEF DESCRIPTION OF THE DRAWINGS

The accompanying drawings, which are incorporated in and constitute a part of this specification, illustrate at least one exemplary embodiment of the invention. In the drawings.

DESCRIPTION OF THE EMBODIMENTS

Reference will now be made in detail to exemplary embodiments of the invention, examples of which are illustrated in the accompanying drawings. Wherever possible, the same reference numbers are used in the drawings and the description to refer to the same or like parts, and the same reference numbers with alphabetical suffixes or numerical prefixes are used to refer to similar parts.

In accordance with certain embodiments, a biological testing device is provided. In one aspect, the biological testing device may perform nucleic acid amplification. In certain embodiments, the biological testing device includes a light source, a light detection device, and a lens. In various embodiments, the biological testing device may also include a sample block, a heated cover, a sample well tray, a seal for covering openings of the sample wells in the sample well tray, a light refractor, a light reflector, or a filter, among other components.

Figure 1:
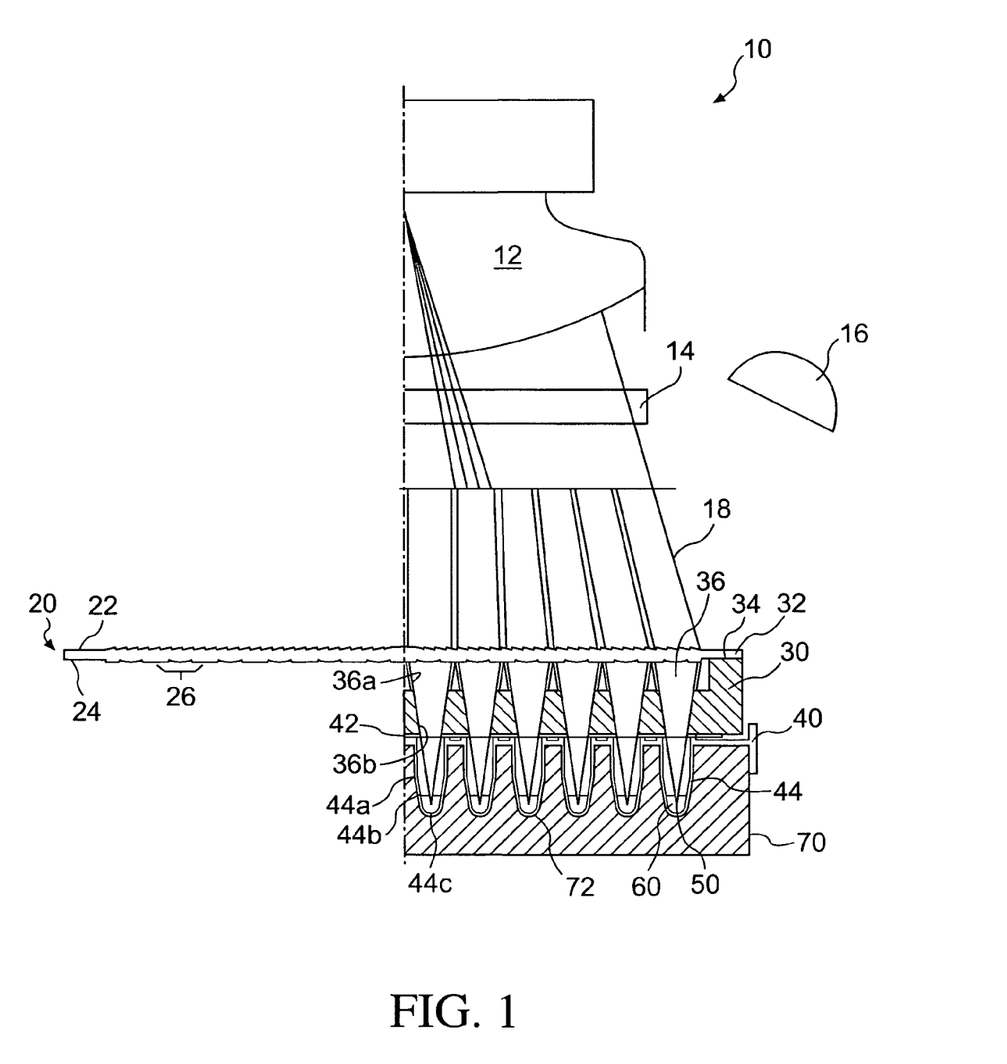
FIG. 1 is a partial section view of a biological testing device according to an exemplary embodiment of the invention.

In FIG. 1, a generally schematic view is shown that is representative of a biological testing device 10 according to an embodiment of the invention. Testing device 10 may be any type of device configured to perform nucleic acid amplification. One common method of performing nucleic acid amplification of biological samples is polymerase chain reaction (PCR). Various PCR methods are known in the art, as described in, for example, U.S. Pat. Nos. 5,928,907 and 6,015,674 to Woudenberg et al., the complete disclosures of which are hereby incorporated by reference for any purpose. Other methods of nucleic acid amplification include, for example, ligase chain reaction, oligonucleotide ligations assay, and hybridization assay. These and other methods are described in greater detail in U.S. Pat. Nos. 5,928,907 and 6,015,674.

In one embodiment, the thermal cycling device performs real-time detection of the nucleic acid amplification of the samples during thermal cycling. Real-time detection systems are known in the art, as also described in greater detail in, for example, U.S. Pat. Nos. 5,928,907 and 6,015,674 to Woudenberg et al., incorporated herein above. During real-time detection, various characteristics of the samples are detected during the thermal cycling in a manner known in the art. Real-time detection permits more accurate and efficient detection and monitoring of the samples during the nucleic acid amplification.

In accordance with various embodiments, the testing device may include a light or radiation source. As embodied herein and shown in FIG. 1, the testing device includes a light source 16 for directing light onto a plurality of biological samples. The biological samples may be positioned in any type of known sample-receiving member. In the embodiment shown in FIG. 1, the samples 60 are located in sample wells 44 of sample well tray 40. Light source 16 may be any conventional type of light source suitable for biological testing, such as a quartz bulb, a laser, (e.g. an argon ion laser), or an LED, for example. Light emitted from light source 16 may be aimed directly toward sample well tray 40, or light source 16 could be aimed at a beam splitter (not shown) that then may redirect at least a portion of the light toward sample well tray 40.

In accordance with various embodiments, biological testing device 10 includes an optical detection system. As embodied herein and shown in FIG. 1, an optical detection device 12 is positioned above the sample well tray 40. The optical detection system 12 is configured to detect and monitor the characteristics of the samples in the sample well tray 40 during the testing. Suitable structures and methods for the optical detection device 12 are well known in the art. The optical detection device may use any known structure or method. In one example, the optical detection device could include a CCD camera, in a manner known in the art. Likewise, the optical detection device may include any other type suitable for use with the thermal cycling device of the present invention.

In certain embodiments, a filter 14 may be provided for filtering the light reflected from the sample and allowing only a predetermined range of light waves to enter the optical detection device 12. Other elements known to be included in detecting devices may be included in testing device 10, such as a prism, a grating, a mirror, or a spectrograph, among others.

In accordance with various embodiments, a seal may be provided for the sample well tray. In one embodiment shown in FIG. 1, sample well tray 40 is covered by a film 42 for sealing the various sample wells 44 and for aiding in minimizing contamination of biological samples 60. Film 42 may be provided with an adhesive on the side facing sample well tray 40 to secure it in place. The film may be made out of any known material suitable for use with a sample well tray. Lenses may be part of the film to provide increased numerical aperture.

In accordance with various embodiments, the biological testing device can include a heated cover. In the embodiment shown in FIG. 1, a cover 30 is located above film 42. As shown in FIG. 1, cover 30 includes a lip 32 around its perimeter. Lip 32 may be continuous or it may also be discontinuous. Lip 32 is raised above surface 34 onto which a lens 20 may be placed. In combination, lip 32 and surface 34 may serve to locate and hold lens 20 in a desired position in relation to cover 30. Cover 30 also includes a plurality of openings 36, with each opening being positioned over one of sample wells 44 to allow light to pass through cover 30 and into biological samples 60 in the sample wells 44. As depicted in FIG. 1, openings 36 taper from an upper edge 36a to a lower edge 36b. In certain embodiments, cover 30 may be heated to augment heating of biological samples 60 provided by a sample block 70. Acting as a heated cover, cover 30 may also serve a function to reduce condensation within the system.

In the embodiment shown, cover 30 rests on film 42, which in turn rests or is adhered to sample well tray 40. Sample well tray 40 may be any member utilized in biological testing to hold one or more samples. In the embodiment shown in FIG. 1, sample well tray 40 includes a plurality of sample wells 44. Sample wells 44 comprise an upper portion 44a that has a substantially cylindrical shape and a tapered lower portion 44b that ends in a rounded bottom portion 44c.

Biological testing device 10 may be configured for use with any type of sample well tray, including, for example, 96-well sample well trays, 384-well sample trays, and microcard sample trays. The size and shape of these sample well trays are well known in the art. Examples of 96-well sample well trays suitable for use in the present invention are described in WO 00/25922 to Moring et al., the complete disclosure of which is hereby incorporated by reference for any purpose. Examples of sample well trays of the microcard type suitable for use in the present invention are described in WO 01/28684 to Frye et al., the complete disclosure of which is hereby incorporated by reference for any purpose, WO97/36681 to Woudenberg et al., the complete disclosure of which is hereby incorporated by reference for any purpose, U.S. application Ser. No. 09/897,500, filed Jul. 3, 2001, assigned to the assignee of the present invention, the complete disclosure of which is hereby incorporated by reference for any purpose, and U.S. application Ser. No. 09/977,225, filed Oct. 16, 2001, assigned to the assignee of the present application, the complete disclosure of which is hereby incorporated by reference for any purpose. Sample well trays having any number of sample wells and sample well sizes may also be used with the thermal cycling device of the present invention. In the example shown in the figures, the volume of the sample wells may vary anywhere from about 0.001 microliters to thousands of microliters, with a volume ranges, for example, of between 1.0 to 500 microliters or 10 to 50 microliters.

In the embodiment shown in FIG. 1, sample well tray 40 includes a plurality of sample wells 44 for holding biological samples 60. In the example shown in FIG. 1, each sample well comprises an upper cylindrical portion 44a and a tapered portion 44b that ends in a rounded bottom portion 44c. It is well understood that the sample wells may have any known size, shape, or configuration.

In accordance with various embodiments, the testing device may include a sample block. As embodied herein and shown in FIG. 1, sample well tray 40 is configured to mount onto sample block 70. Sample block 70 may be any sample block known in the art that is used to receive a sample well tray and provide heating and/or cooling of biological samples 60. Sample block 70 may be machined or cast of a material suitable for conducting heat to sample tray 40 and includes a plurality of sample well openings 72 equal in number to a number of sample wells 44 of sample tray 40.

As mentioned above, lens 20 may rest on, or be otherwise adjacent to, cover 30 and may perform the function of both focusing and collimating light emitted from and/or directed to samples 60. Lens 20 comprises at least two surfaces: a first surface 22 facing detection device 12 and a second surface 24 facing sample well tray 40. As used herein, "surface" is intended to broadly define a generally planar external portion of the lens that may include a plurality of sub-surfaces formed into the surface with the various sub-surfaces providing the desired overall lens characteristics. First surface 22 comprises a Fresnel lens for collimating light and second surface 24 includes a matrix 25 having a plurality of focusing lens portions or segments 26 equal to the number of sample wells 44. Each focusing lens portion or segment 26 is defined as the portion of surface 24 configured to focus light into an individual sample 60. Lens 20 will be described in greater detail below.

Figure 2:
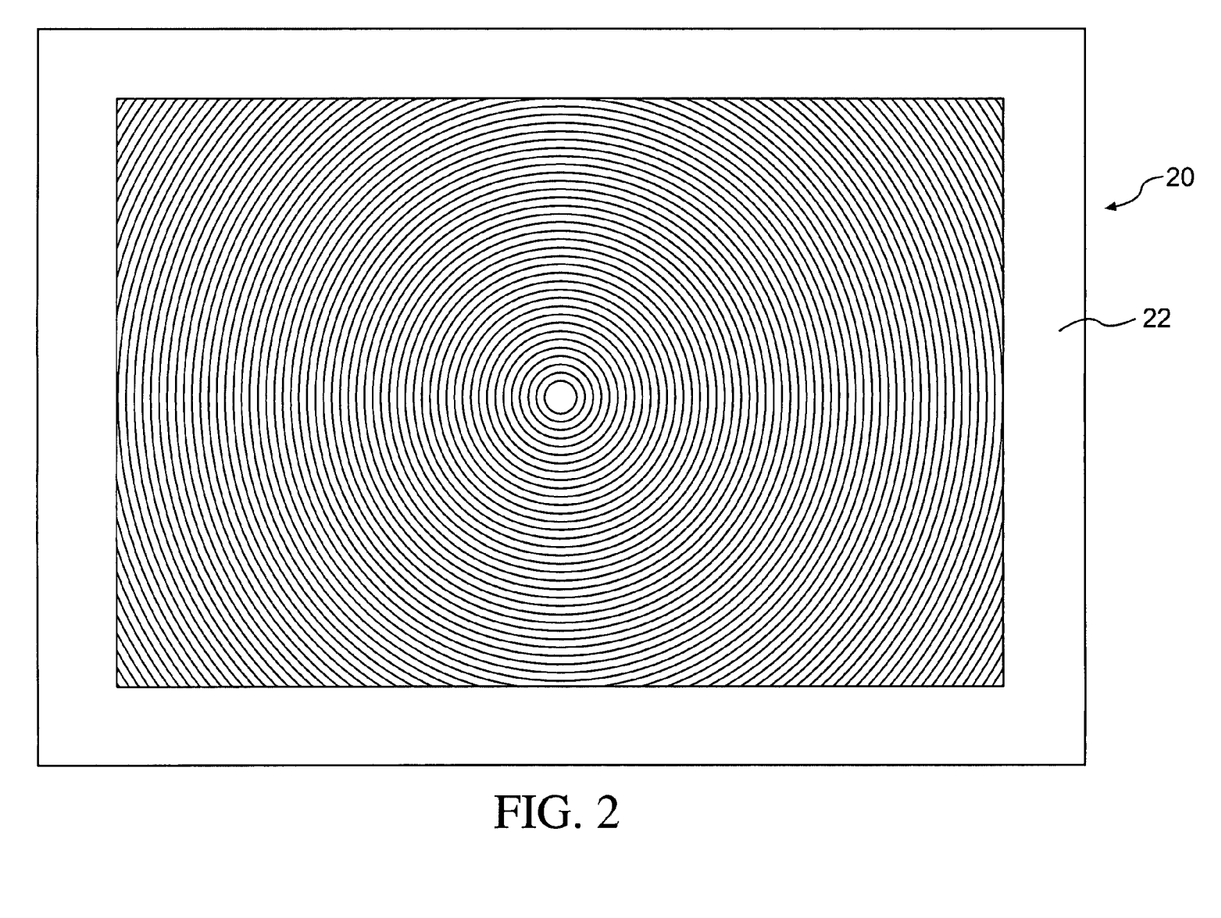
FIG. 2 is a plan view of a first side of a single-piece lens depicted in FIG. 1.

As can be seen in FIG. 1, light is emitted from light source 16 and contacts first surface 22 of lens 20. FIG. 2 shows the configuration of first surface 22. This configuration may be a Fresnel lens of the type manufactured by the Fresnel Technologies of Fort Worth Tex. There are at least two basic types of Fresnel lenses. The first has a constant pitch with increased depth toward the outer edges and the second has a uniform depth. Either configuration could be used, but the uniform depth Fresnel lens is depicted in the embodiment shown in FIGS. 1-4.

Figure 3:
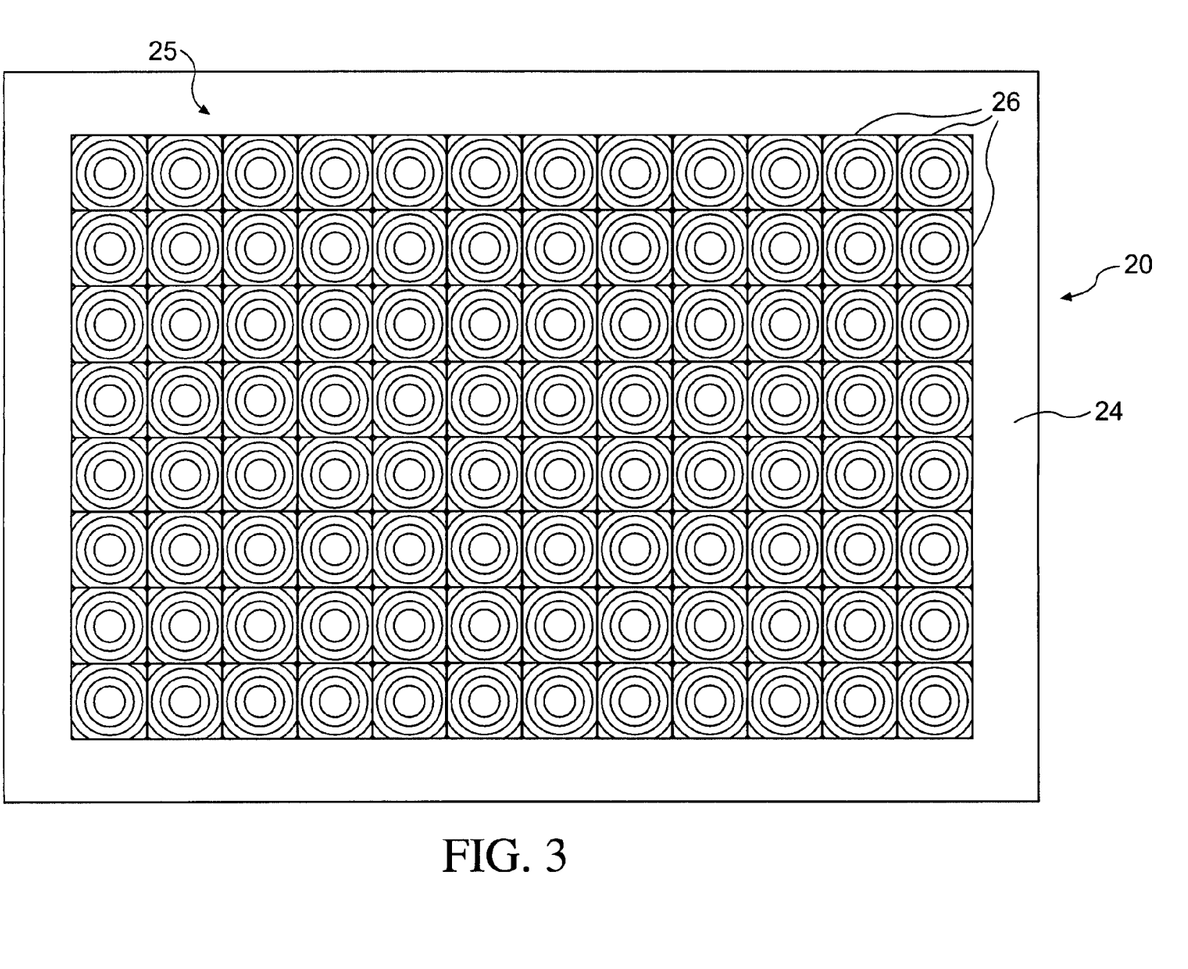
FIG. 3 is a plan view of a second side of the single-piece lens of FIG. 2.

In the embodiment shown, first surface 22 is used to substantially collimate light beams 18 so that the light is directed toward each of the rows or columns of sample wells 44 of sample well tray 40. Light beams 18 then pass through to a second surface 24 of lens 20 which has formed on its surface a matrix 25 of focusing lenses (or focusing lens segments) 26 as shown in FIG. 3 for focusing light into each of biological samples 60 located in sample wells 44. Radiation, for example fluorescent radiation, from the samples 60 may pass through lens 20 in a reverse direction. Lens 20 serves to collect the reflected light and direct it toward detecting device 12.

Figure 4:
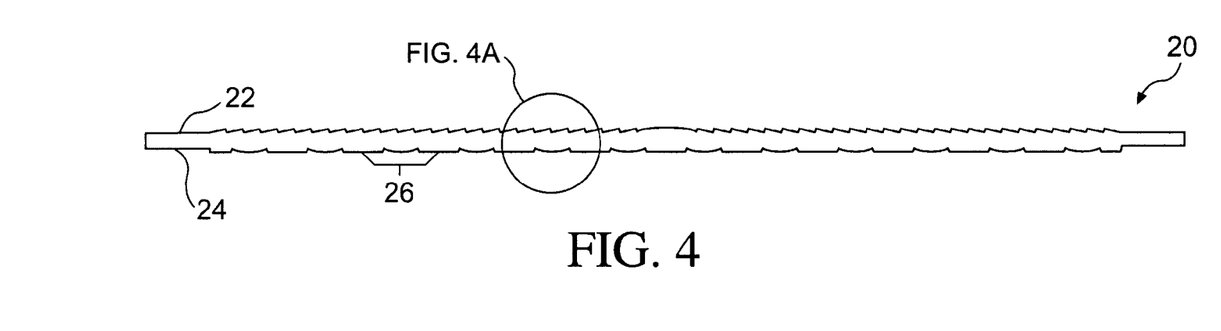
FIG. 4 is a section view of the single-piece lens of FIG. 2.
Figure 4A:
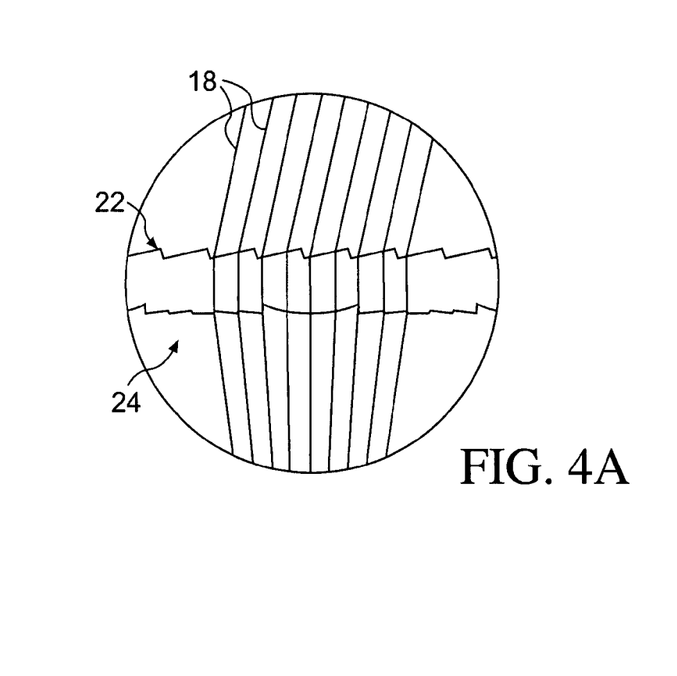
FIG. 4A is a close-up view of the circled portion of FIG. 4.

As seen in FIG. 4A in a close-up view of light passing through one of the focusing lens segments 26, light beams 18 pass through first side of lens 22 and are substantially collimated. As beams 18 pass through the second surface 24, they are focused toward the desired sample location. As depicted, each lens segment 26 comprises an individual Fresnel lens of concentric rings to accomplish the focusing. Although a Fresnel focusing lens is shown, other focusing lenses that may be formed into the second surface of the lens may be suitable as well.

In the embodiment shown in FIGS. 1-4, lens 20 integrates both the collimating function of side 22 and the focusing function of side 24 into the lens. First, as can be seen in FIG. 4, by forming the focusing lens segments 26 into the second surface 24 of lens 20, focusing lens segment 26 may occupy a substantial portion of the area over its associated sample well 44. This expanded lens allows for a maximum amount of light to pass into each of the samples 60. In addition, focusing lens segments 26, being formed into the second surface 24, are fixed in relation to each other, thus minimizing the potential for movement between respective focusing lens segments.

Also, by integrating Fresnel lens side 22 and focusing lens side 24 into opposing surfaces of lens 20, the potential for misalignment may be reduced or even eliminated between the collimating and focusing functions. Because Fresnel lens side 22 and focusing lens side 24 of lens 20 are fixed in relation to each other, a correct alignment with respect to each other may be desirably maintained.

As described herein and shown in FIG. 1, heated cover 30 may also provide a mounting surface 34 for lens 20 that may assist in maintaining a proper alignment between lens 20 and sample well tray 40. Further enhancing this alignment, lens 20 can optionally be fastened to heated cover 30 by any fastening means known in the art (e.g., a mechanical device such as clips, clamps, screws, adhesives, etc.) so as to further reduce movement and alignment problems between lens 20 and heated cover 30.

In another aspect, lens 20 may be configured so that one or more of lens segments 26 may provide light of a different intensity as compared to another of lens segments 26. As mentioned above, light source 16 may be a quartz light. Light sources such as this often emit light of focused intensity that is concentrated at a central area of lens 20. As one moves toward the periphery of the lens assembly, the light emitted by light source 16 may be diminished. To compensate for this, one or more of focusing lens segments 26 may be configured in such a way as to substantially equalize the intensity of the light that is focused into each of the samples 60.

In certain embodiments, for example, the focusing lens segments 26 located near the center of lens 20 could be molded in a fashion whereby the optics of the individual focusing lens segments could be varied so that they allow less light to pass through than focusing lens segments located at a periphery of lens 20. Any or all of focusing lens segments 26 could be altered in a similar fashion to correspond to varying intensities of light directed onto the grid of lens 20. This could also be accomplished, for example, by masking a portion of selected focusing lens segments to reduce the amount of light that passes through them. The term "mask(ing)" as used herein is intended to mean reducing or completely inhibiting the light transmission capability of at least a portion of each of the focusing lens(es). This could be accomplished by applying a coating, for example paint, that would occlude at least a portion of the focusing lens segment. Masking could also include applying an adhesive material such as tape to a portion of the focusing lens segment for reducing the amount of light that passes through the lens. This masking could be done in various amounts throughout the lens matrix to achieve the desired intensity of light into each of the samples 60.

Lens 20 may be made by any suitable method. For example, it is contemplated that lens 20 could be manufactured by injection or compression molding. Lens 20 could be made of a non-fluorescing clear polycarbonate, for example. Testing devices using a heated cover, such as heated cover 30, often operate at temperatures approaching or even exceeding 80° C. For such high-temperature devices, a material such as Lexan is suitable for lens 20. Devices operating at lower temperatures, for example at or near 60° C., may include a lens made of any number of materials such as acrylics, styrenes, polyethylenes, polycarbonates, polypropylenes, or any other transparent plastic that may be suitable. Other materials, such as glass or quartz may also be contemplated that would provide the same or similar characteristics as the ones included herein.

Although lens 20 is shown in a 12×8 grid configuration comprising 96 focusing lens segments, it is to be understood that this lens configuration could be modified into substantially any configuration to correspond with various sample well tray configurations or shapes. For example, lens 20 could have 4, 8, 12, 24, 384, 768 1536, 3072, 6144, or more focusing lens segments. Lens 20 could also be formed in various shapes other than a rectangle so as to conform to a shape of a sample well tray.

FIGS. 1-4 show the lens 20 in combination with a heated cover 30 and sample well tray 40 with a plurality of sample wells 44. In certain embodiments, lens 20 can be used with other sample testing devices that may or may not have a heated cover. For example, FIG. 5 shows the lens 20 in use with a sample-testing device that does not have a heated cover.

Figure 5:
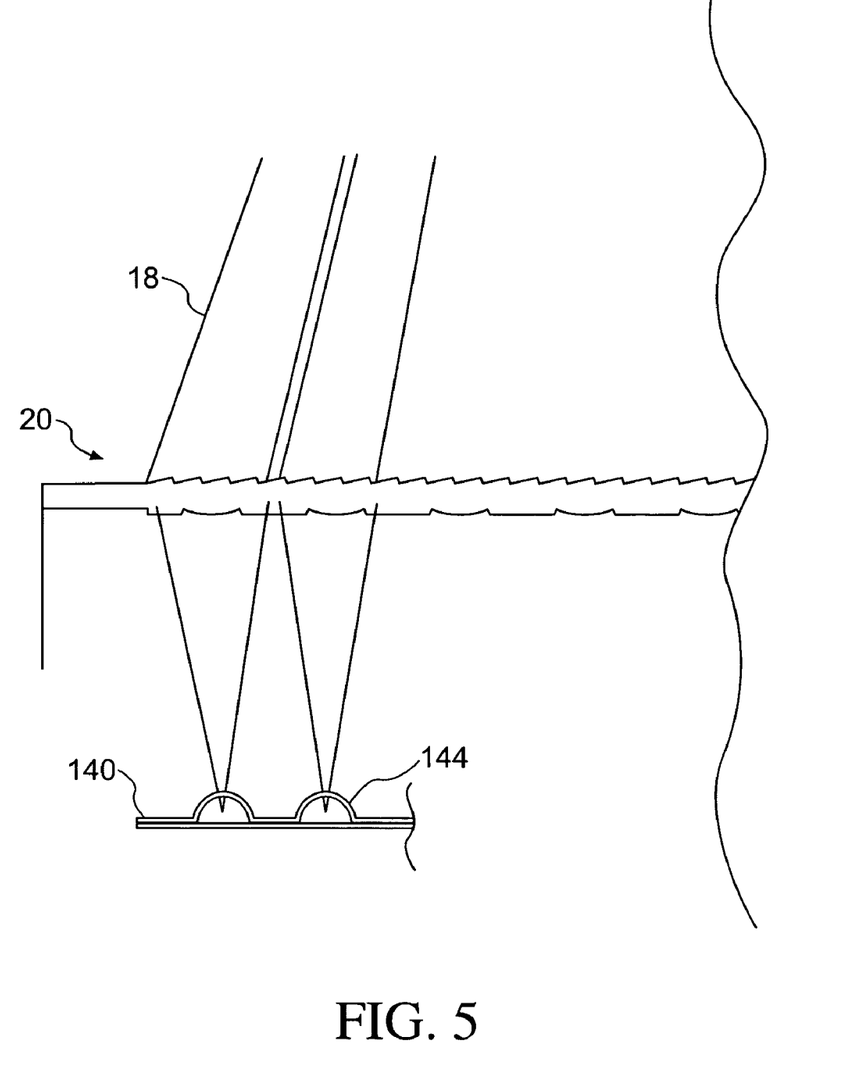
FIG. 5 is a partial section of the lens of FIG. 1 in combination with a microcard sample tray.

In FIG. 5, lens 20 is used in combination with a microcard sample tray 140. Microcard sample trays are known in the art as discussed above. In the embodiment shown in FIG. 5, microcard sample tray 140 includes a plurality of sample wells or chambers 144 configured to contain a sample for testing. Chambers 144 may align with a matrix of lenses in a fashion similar to the sample well tray 40 of FIG. 1. Microcard sample tray 140 can have any of the various configurations, sizes and shapes known in the art. In the embodiment shown in FIG. 5, the microcard sample tray is used without a heated cover. Microcard sample tray 140 may also be used with a heated cover. In various embodiments, the microcard cover can provide focusing lens segments or diffractive elements. Such embodiments can be less susceptible to temperature degradation. The focusing lens cover for a microcard is described at U.S. Pat. No. 6,272,939.

In various embodiments, conventional lenses can integrate both the collimating function and focusing function with an element on one side. The lenses can be disposed on lines between axial object points and each samples axial point. In such an embodiment, the pitch of lenses can be varied based on axial location to emulate the effect of the Fresnel lens in previously described embodiments. However, the path in such an embodiment is not normal to the sample, thereby providing limited penetration into the depth of outlying wells since the wells are parallel and not radial. Hence, it is desirable to use this embodiment where the wells are not deep wells and the heated cover is not thick.

In various embodiments, one side of the lens 20 can be a diffractive optical component. The lens can integrate both the collimating function and focusing function with a diffractive or refractive element on one side. Diffraction optical components are optical elements that use diffraction (the bending of light as it passes an obstruction) to control wavefronts. Diffractive optical elements include but are not limited to diffraction gratings, surface-relief diffractive lenses, holographic optical elements and computer-generated holograms. Diffractive optical elements can be formed using, for example, at least one of diamond machining, interference of coherent beams (holography), injection molding, reactive ion etching, fixed and adjustable spatial light modulators, including, for example, liquid crystal spatial light modulators, and advanced microlithographic techniques.

In various embodiments, the diffractive optical component is configured to receive light of a given shape and intensity distribution, and to redistribute the light to produce a desired shape and/or intensity distribution. In certain embodiments, the redistribution of the light can be based on optical diffraction alone. In certain embodiments, the redistribution of the light can be based on optical diffraction in combination with other optical processes, such as optical reflection and/or refraction. Optical refraction is a change in the direction of propagation when a wave passes from one medium to another of different density or refractive index.

In various embodiments, the diffractive optical component is configured to regulate the received light and compensate for at least one of light intensity distributions and shapes of the light due to at least one of the light source and interaction of the light with optical elements of the apparatus. As a non-limiting example, the diffractive optical component can be configured to redistribute the Gaussian intensity profile of light from a laser to another intensity profile, such as a more uniform top-hat intensity profile. As another non-limiting example, the diffractive optical component can be configured to redistribute the spatially circular profile of light from a light source to another shape, such as a rectangular profile. As yet another non-limiting example, the diffractive optical component can be configured to compensate for aberrations, such as spherical and chromatic aberrations, such as those caused by the interaction of the light with optical elements of the apparatus.

In various embodiments, the diffractive optical element may regulate the received light by reshaping the cross sectional profile of the light. For example, the diffractive optical element may reshape the received light from a generally circular or elliptical cross section to form regulated light having a generally rectangular cross section. Of course, the diffractive optical element may be configured to regulate received light having shapes other than circular, and to generate regulated light having shapes other than rectangular.

Figure 13A:
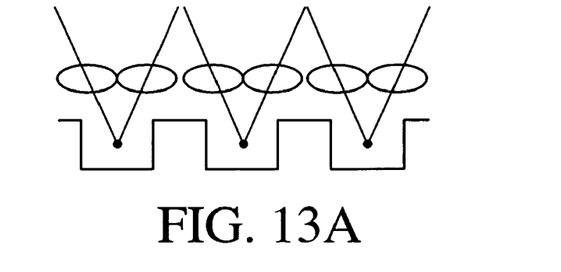
FIGS. 13A-13C are section view of off-axis illumination systems showing correspondence of lenses to wells in FIG. 13A, misalignment in FIG. 13B, and the non-alignment of more lenses than wells in FIG. 13C.
Figure 13B:
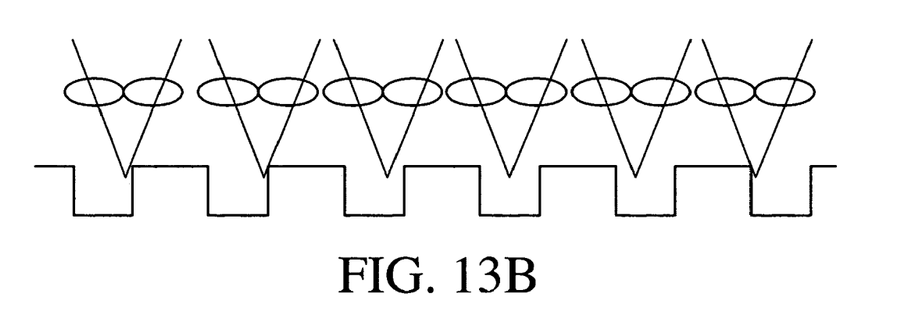
Figure 13C:
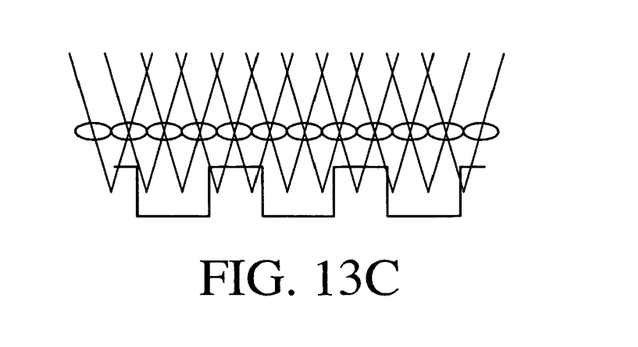

In various embodiments, the lens can include more focusing lens segments than sample wells or chambers. Each sample well or chamber can have more than one focusing lens segment associated with it. This can reduce the effect of alignment on a lens where there is a one-to-one correspondence between focusing lens segments and sample wells or chambers. In various embodiments, a plurality of focusing lens segments can be associated with each sample well or chamber. In various embodiments, the lens can include more focusing lens segments than required to image the entire substrate into which the sample well or chambers are located. In various embodiments, the focusing lens segments can be part of the well structure instead of being part of the lens. In various embodiments, some of the focusing lens segments can focus light from more than one well or chamber. The light detection device can be configured to identify either by disregarding or giving a lower weight to the focusing lens segments that focus light from more than one well or chamber. In various embodiments, some of the focusing lens segments can focus light partly from a well or chamber and partly from the substrate between wells or chambers. The light detection device can be configured to disregard or give a lower weight to the focusing lens segments that focus light partly from a well or chamber and partly from the substrate between wells or chambers. FIG. 13A illustrates an aligned array of focusing lens segments with the biological samples in wells where one focusing lens segment corresponds to the excitation light in an off-axis illuminated system. The term "off-axis" as used herein, refers to illumination that is not perpendicular to the face of the samples. FIG. 13B illustrates an misaligned array of focusing lens segments with the biological samples in wells where one focusing lens segment corresponds to the excitation light in an off-axis illuminated system. FIG. 13C illustrates a off-axis illuminated system with multiple focusing lens segments for excitation light where effects of alignment can be reduced by disregarding light not directed into the wells. There is non-alignment, but that does not impede light entering the wells because there are more lenses than wells. In various embodiments, four or six light sources can correspond to each sample well similar to FIG. 13C. The excitation light sources pass though the six hexagonal lenses disposed about a single central lens of the hexagon, and emission light passes through the central lens of the hexagon en route to the detector.

In various embodiment, multiple focusing lens segments corresponding to a biological sample, for example in a well or chamber, can provide substantially equal light collection from the biological sample as single focusing lens segments corresponding to a biological sample by providing multiple optical paths into a single sample. This can be improved by increasing the well width to depth ratio. In various embodiments, the amount of optical crosstalk between emission light from some focusing lens segments can be reduced by avoiding aligning the focusing lens segments to the biological samples and by selecting lens segments that are sufficiently small to prevent alignment.

In various embodiments, the focusing lens segments can be an array of Fresnel lenses. The first surface and second surface could both be Fresnel lenses. The first surface including one Fresnel lens and the second surface including an array of Fresnel lenses. In various embodiments the first surface can be a Fresnel lens and the second surface can be an array of convex lenses. In various embodiments, the lenses can be constructed of any transparent material such as plastic or glass.

Figure 6:
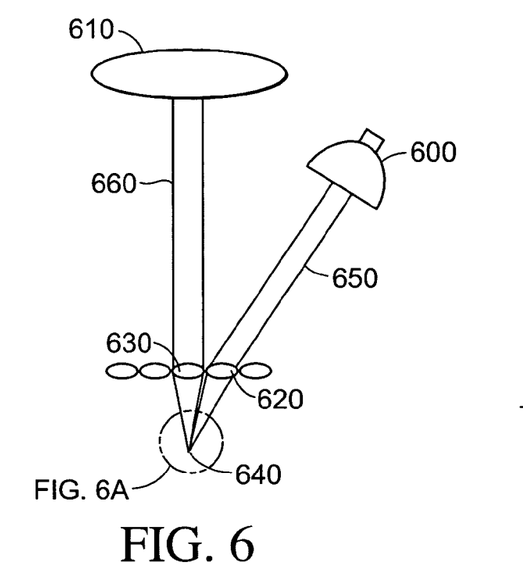
FIG. 6 is a section view of an off-axis illumination system with intersecting excitation and emission light paths.
Figure 6A:
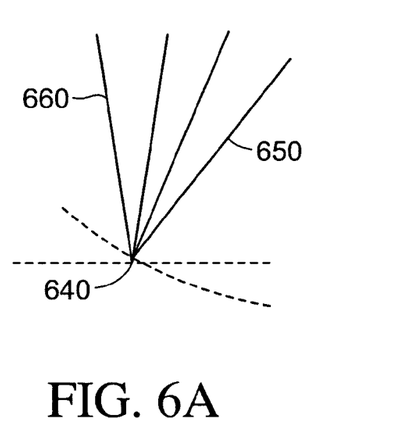
FIG. 6A is a close-up view of the circled portion of FIG. 6.

In various embodiments, the array of focusing lens segments can be configured to provide a spacing between the center of adjacent focusing lens segments that corresponds to the difference in the angle between the emission light path and the excitation light path of an off-axis illumination system. Such a configuration provides substantially intersecting light paths between the excitation light path through a focusing lens segment and the emission light path through an adjacent focusing lens segment. FIG. 6 illustrates an example of off-axis illumination system. Light source 600 provides excitation light that travels through focusing lens segment 620 along excitation light path 650. The emission light collected by collection lens 610 travels through focusing lens segment 630, which is adjacent to focusing lens segment 620, along emission light path 660. The excitation light path 650 intersects with emission light path 660 near the point where both beams are substantially focused 640 depending on angle change. FIG. 6A illustrates a magnified view of substantial point of coincidence 640 where excitation light path 650 and emission light path 660 overlap.

Figure 7:
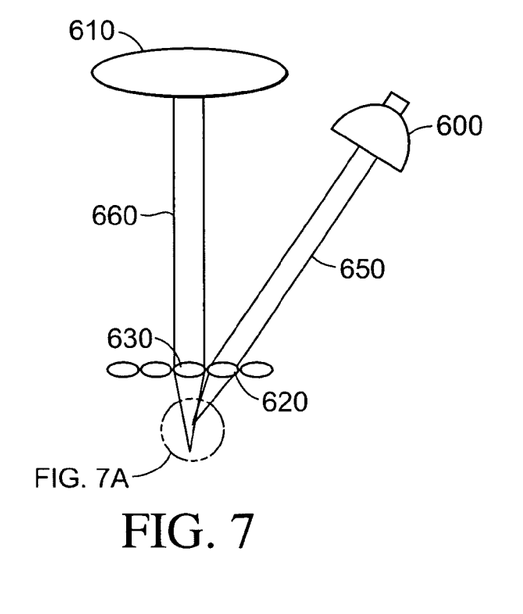
FIG. 7 is a section view of an off-axis illumination system without a point of intersection between the excitation and emission light paths.
Figure 7A:
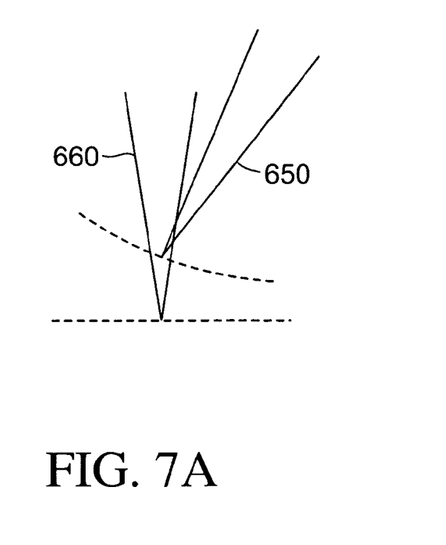
FIG. 7A is a close-up view of the circled portion of FIG. 7.

In various embodiments, due to the natural curved focus field of individual lenses and the dependence of focal length on wavelength, shortening the source-side focus distance can lengthen the off-axis sample-side focus distance because the different optical paths (focal length coming into focusing lens segment) provide better coincidence. If the light source is too far away, then there can be a mismatch of excitation path and emission path such that the two beams are not substantially focused at their intersection point. FIG. 7 illustrates a similar off-axis illumination system as the one illustrated in FIG. 6. FIG. 7A illustrates the lack of coincidence of the excitation light path and emission light path. In various embodiments, the focal length of the focusing lens segments can be reduced to provide correspondence with focusing lens segments not immediately adjacent to the collection lens and light detection device.

Figure 8:
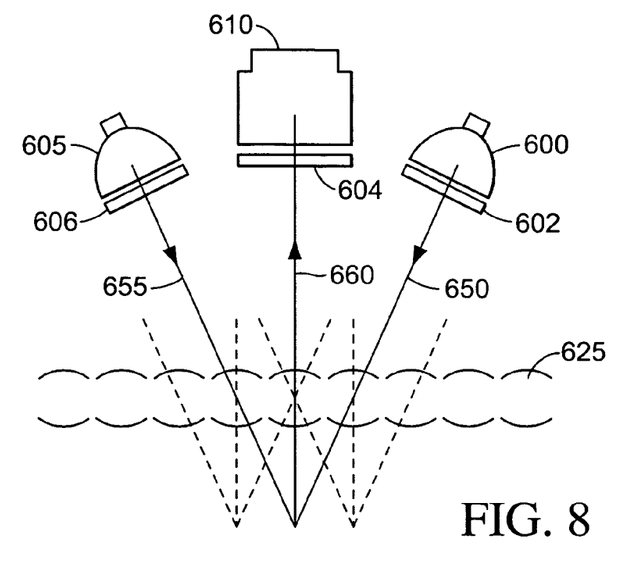
FIGS. 8-8A are section views of off-axis illumination systems with two light sources delivering excitation to each sample well.
Figure 8A:
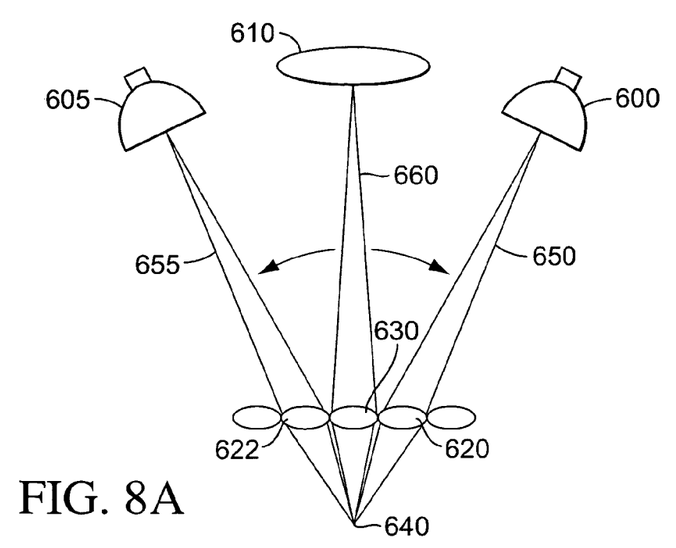

In various embodiments, multiple off-axis light sources can be positioned closer to the array of focus lens segments than the light detection device to provide co-focus of multiple light sources on a single point of coincidence. FIG. 8 illustrates an off-axis illumination system with multiple light sources. This figure shows the components in FIG. 6 with an additional light source 605. The array of focusing lens segments 625 provides the multiple lens segments for the system. The light sources 600 and 605 can be filtered with filters 602 and 606 to control the wavelengths of light used for excitation. The collection lens 610 can also be filtered with filter 604 to control the wavelength of light detected. FIG. 8A illustrates the focus point for the first excitation light path 650 and the second excitation light path 655 as coincident with the emission light path 660. The focus point is the same for the two paths. In various embodiments, the focus points for the two excitation light paths are not exactly the same for the two foci, but instead provide an overlap of substantially similar cone angles, to maximize the coupling between the excitation light paths and emission light path. In various embodiments, alternating focal lengths or pitches can be used so that rays emitted from the focal point of an excitation beam passing through one lens are substantially collimated after passing through an adjacent lens.

Figure 9:
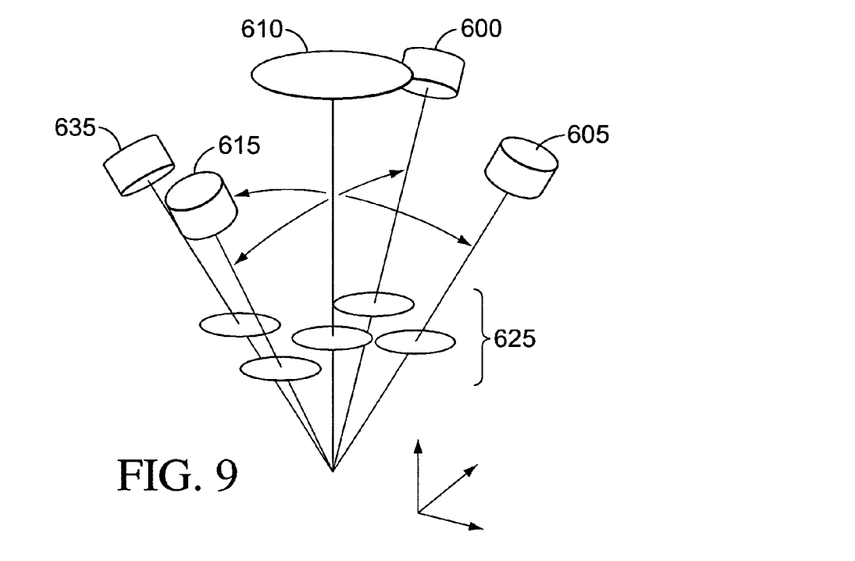
FIG. 9 is a perspective view of an off-axis illumination system with four light sources per sample well.
Figure 10A:
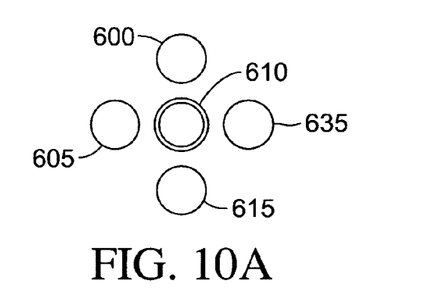
FIGS. 10A-10C are cross-sectional views of configurations of multiple light sources per detector.
Figure 10B:
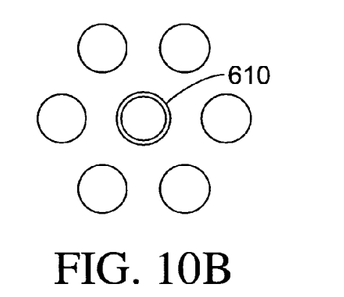
Figure 10C:
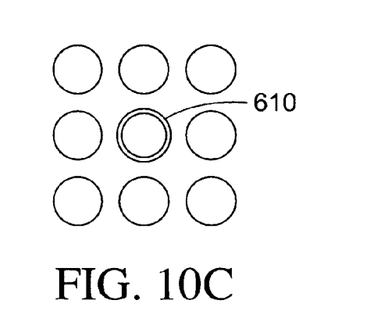
Figure 11A:
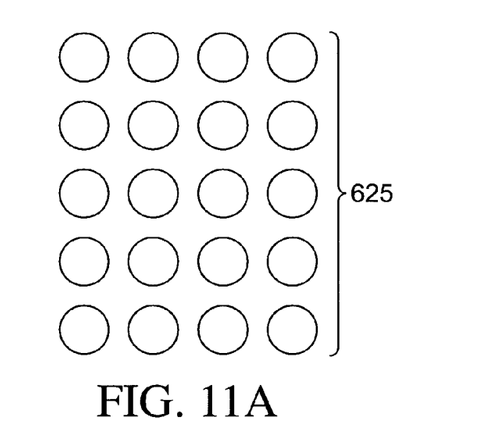
FIGS. 11A-11B are cross-section views of configurations of focusing light segments to correspond to the multiple light sources per detector illustrated in FIG. 10A-10C.
Figure 11B:
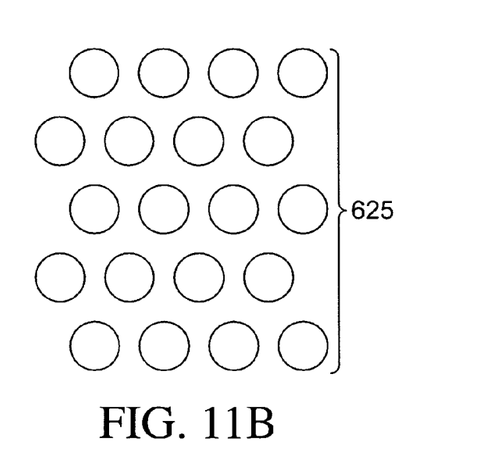
Figure 12:
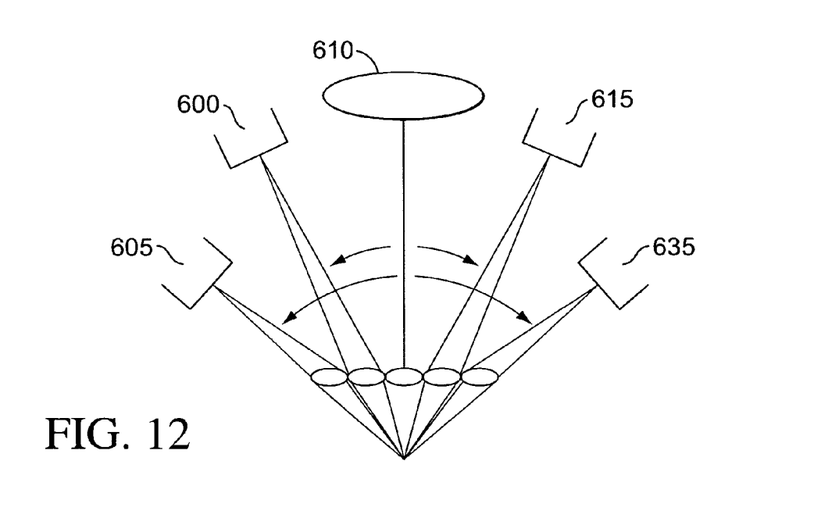
FIG. 12 is a section view of an off-axis illumination system with four light sources per sample well.

In various embodiments, multiple light sources can be positioned around the collection optics. FIG. 9 illustrates multiple light sources 600, 605, 615, and 635 positioned over the array of focusing light segments 625 and around collection lens 610. In various embodiments, the pattern of focusing lens segments can be aligned with the pattern of light sources. In various embodiments, four light sources can be distributed equally around the collection lens and light detection device as illustrated in FIG. 10A, wherein light source 600, 605, 615, and 635 are positioned around collection lens 610. This can correspond to a square rectilinear pattern of focusing lens segments as illustrated in FIG. 11A showing the array of focusing lens segments 625. In various embodiments, six light sources can be distributed equally around the collection lens and light detection device as illustrated in FIG. 10B. This can correspond to a close-packed hexagonal pattern of focusing lens segments as illustrated in FIG. 11B. In various embodiments, eight light sources can be distributed as two sets of four light sources around the light detection device as illustrated in FIG. 1C. This can correspond to a square rectilinear pattern of focusing lens segments as illustrated in FIG. 11B. In various embodiments, additional light sources source can be added by positioning the light sources at the corners and spaced such that the angle in each axis is the same. In various embodiments, additional light sources can correspond to focusing lens segments not immediately adjacent to the collection lens and light detection device, as illustrated in FIG. 12. This can result in an increased angle if the plane of view is rotated 45 degrees.

In various embodiments, in the diffractive system, it is not necessary to separate the collimation and focusing. A single surface can provide both collimation of light and focusing. In various embodiments, the lens with focusing lens segments can be unitary or the refractive element or Fresnel lens can be separate components.

It will be apparent to those skilled in the art that various modifications and variations can be made to the structure. Thus, it should be understood that the invention is not limited to the examples discussed in the specification. Rather, the present invention is intended to cover modifications and variations.

What is claimed is:

1. An optical detection system for a thermal cycling device, comprising:
    at least one light source;
    a light detection device for detecting light received from a plurality of sample wells containing biological samples;
    a lens, the lens comprising a matrix of multiple focusing lens segments, wherein the matrix of multiple lens segments provides more than one focusing lens segment per sample well; and
    at least one of the more than one focusing lens segments per sample well directs light into the sample well.

2. The optical detection system of claim 1, wherein the lens comprises a first surface and a second surface formed on the lens, the second surface substantially opposed to the first surface, wherein the first surface substantially collimates light and the second surface forms the matrix of multiple focusing lens segments.

3. The optical detection system of claim 1, wherein the lens comprises a diffractive optical component.

4. The optical detection system of claim 1, further comprising a Fresnel lens or refractive element.

5. The optical detection system of claim 1, wherein each focusing lens segment is not aligned with each biological sample, and wherein the light detection device is configured to identify the focusing lens segments not corresponding to any biological sample.

6. The optical detection system of claim 1, wherein the light source provides off-axis illumination.

7. The optical detection system of claim 6, wherein adjacent focusing lens segments correspond to an excitation light path and an emission light path.

8. The optical detection system of claim 7, wherein the adjacent focusing lens segments provide a point of substantial coincidence between the excitation light path and the emission light path.

9. The optical detection system of claim 7, wherein the focusing lens segments corresponding to the excitation light paths of multiple light sources are positioned around the focusing lens segments corresponding to the emission light paths of the light detection device.

10. The optical detection system of claim 9, wherein the focusing lens segments are arranged in a square rectilinear pattern.

11. The optical detection system of claim 9, wherein the focusing lens segments are arranged in a close-packed hexagonal pattern.

12. A thermal cycling system, comprising:
a sample block assembly configured to receive a plurality of sample wells; each sample well containing a biological sample, wherein the sample block is configured for thermally cycling the biological samples;
a lens, the lens comprising a matrix of multiple focusing lens segments wherein the matrix of multiple lens segments provides more than one focusing lens seoment per sample well; and and wherein at least one of the more than one focusing lens segments per sample well directs light into the sample well;
a light source configured to provide excitation light to the lens; and
a light detection device configured to detect emission light from the lens.

13. The thermal cycling system of claim 12, wherein the lens comprises a first surface and a second surface formed on the lens, the second surface substantially opposed to the first surface, wherein the first surface substantially collimates light and the second surface forms the matrix of multiple focusing lens segments.

14. The thermal cycling system of claim 13, wherein the first surface is a diffractive optical component or a Fresnel lens.

15. The thermal cycling system of claim 12, wherein the lens comprises at least one non-luminescent material chosen from glass, acrylics, styrenes, polyethylenes, polycarbonates, and polypropylenes.

16. The thermal cycling system of claim 12, further comprising a heated cover assembly, wherein the heated cover assembly comprises a lens system.

17. The thermal cycling system of claim 16, wherein the sample block assembly is configured to mate with the heated cover assembly.

18. The thermal cycling system of claim 17, wherein the heated cover assembly comprises a fastening device configured to mount the lens system.

19. A thermal cycling system, comprising:
means for focusing excitation light into each of the plurality of biological samples;
means for providing the excitation light;
means for detecting emission light from the biological samples; and
means for containing the biological samples,
wherein the means for focusing is not aligned to provide one-to-one correspondence with the means for containing the biological samples.

20. The thermal cycling system of claim 19, further comprising means for collimating the emission light from the biological samples.

* * * * *